(12) United States Patent
Liu et al.

(10) Patent No.: US 9,785,047 B2
(45) Date of Patent: Oct. 10, 2017

(54) METHOD AND DEVICE FOR MEASURING LARGE-AREA AND MASSIVE SCATTERED FIELD IN NANOSCALE

(71) Applicant: Huazhong University of Science and Technology, Wuhan (CN)

(72) Inventors: Shiyuan Liu, Wuhan (CN); Weichao Du, Wuhan (CN); Chuanwei Zhang, Wuhan (CN); Yinyin Tan, Wuhan (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 154 days.

(21) Appl. No.: 14/754,759

(22) Filed: Jun. 30, 2015

(65) Prior Publication Data

US 2016/0187248 A1  Jun. 30, 2016

(30) Foreign Application Priority Data

Dec. 31, 2014  (CN) .......................... 2014 1 0855944

(51) Int. Cl.
  *G03F 7/00*   (2006.01)
  *G01B 11/06*  (2006.01)
  *G01B 11/24*  (2006.01)
  *G01N 21/21*  (2006.01)

(52) U.S. Cl.
  CPC ............ *G03F 7/00* (2013.01); *G01B 11/0641* (2013.01); *G01B 11/24* (2013.01); *G01B 2210/56* (2013.01); *G01N 2021/214* (2013.01)

(58) Field of Classification Search
  CPC ........... G01N 2021/214; G01N 21/211; G01B 11/2531
  See application file for complete search history.

(56) References Cited

U.S. PATENT DOCUMENTS

| | | | | |
|---|---|---|---|---|
| 8,456,639 B2* | 6/2013 | Krishnan | ................ | G01J 3/021 356/237.1 |
| 2004/0017561 A1* | 1/2004 | Meeks | ............... | G01B 11/0616 356/237.3 |
| 2011/0116694 A1* | 5/2011 | Gareau | ............. | G01N 21/6458 382/128 |
| 2014/0375981 A1* | 12/2014 | Wang | ................ | G01N 21/9501 356/51 |

* cited by examiner

*Primary Examiner* — Shawn Decenzo
(74) *Attorney, Agent, or Firm* — Matthias Scholl, PC; Matthias Scholl

(57) ABSTRACT

A device for measuring a large-area and massive scattered field in nanoscale. The device includes a polarization state generator disposed on an output optical path of a laser source, a polarization state analyzer operating to demodulate a polarized light beam emitted thereon, a first objective lens and a first lens disposed on an optical path of a sample stage, and a scanning mirror disposed on an optical path in front of or at the rear of the polarization state generator.

15 Claims, 6 Drawing Sheets

METHOD AND DEVICE FOR MEASURING LARGE-AREA AND MASSIVE SCATTERED FIELD IN NANOSCALE

CROSS-REFERENCE TO RELATED APPLICATIONS

Pursuant to 35 U.S.C. §119 and the Paris Convention Treaty, this application claims the benefit of Chinese Patent Application No. 201410855944.7 filed Dec. 31, 2014, the contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a method and a device for rapidly measuring a large-area and massive scattered field in nanoscale.

Description of the Related Art

Conventional methods for measuring the three-dimensional profile parameters in IC manufacturing include: a scanning electron microscope (SEM), an atomic force microscope (AFM), a transmission electron microscopy (TEM), a conventional optical microscope (OM), an optical scattering device. The scanning electron microscope (SEM) and the transmission electron microscopy (TEM) are non-contact measurement and feature very high horizontal and vertical revolution. However, the samples are destructed during preparation for measurement, and it is impossible to conduct on-line and massive measurement due to limitation on a vacuum environment during measurement.

The atomic force microscope (AFM) is a kind of contact measurement using surface probes, but samples are easily destructed during measurement, and a scanning and measuring speed is comparatively slow. The conventional optical microscope (OM) cannot be used for measurement of nanometer-scale structure as being limited by optical revolution. The optical scattering device is referred to as an optical critical dimension (OCD) measurement instrument, a basic principle thereof is to project polarized light on surface of a measured structure, to obtain variation of a polarization state of the polarized light after reflection by measuring zeroth-order diffraction light of the measured structure, and to extract information of the measured structure by solving an inverse scattering problem.

However, as shown in FIG. 1, the conventional optical scattering device cannot collect diffraction light other than zeroth-order diffraction light of a measured sample, which makes information collection thereof incomplete. Since only reflection of the zeroth-order diffraction light with periodic structure is used, the device can only measure simple periodic structure with a small high-aspect-ratio deep structures (such as a one-dimensional grating structure and a two-dimensional grating structure) based on the current model-based measurement method. In addition, limited by spot size (a size of approximately 50 μm) during measurement, a few statistical parameters of the periodic structure, such as a critical dimension, a height, a side angle and so on, can be obtained within a range of the spot, which significantly restricts wider application of the optical scattering device, and makes it impossible to apply it to measurement of complex three-dimensional nanometer structure.

SUMMARY OF THE INVENTION

It is an objective of the invention to provide a device and a method for rapidly measuring a large-area and massive scattered field in nanoscale that are capable of obtaining three-dimensional profile parameters of a measured sample by providing a scanning mirror for changing an incident angle of a light beam, along with an objective lens and an imaging lens thereby obtaining distribution of a large-area scattered field of the measured sample and sixteen Mueller matrix elements of the scattered field. In addition, this invention can rapidly obtain a large-area scattered field of the measured sample in nanoscale, and thus enable rapid and accurate measurement of a complex three-dimensional nanometer structure.

To achieve the above objectives, in accordance with an aspect of the invention, provided is a device for rapidly measuring a large-area and massive scattered fields in nanoscale, comprising: a polarization state generator (PSG) being disposed on an output optical path of a laser source, which operates to modulate a light beam emitted thereon and obtain a light beam with a polarization state; a polarization state analyzer (PSA) operating to demodulate a emitted polarized light beam which contains information of a measured sample thereby obtaining information of the measured sample; a first objective lens and a first lens being disposed on an optical path of a sample stage; and a scanning mirror being disposed on an optical path in front of or at the rear of the PSG, and operating to vary an incident angle of the polarized light beam emitted to the lens, a position thereof focused on the back focal plane (BFP) of the first objective lens, and thus an angle of a light beam parallel emitted to the sample from the first objective lens, thereby obtaining a scattering distribution image of the measured sample at different incident angles, and enabling rapid and accurate profile measurement of the measured sample in nanoscale by obtaining Mueller matrix at different scattered fields; the measured sample on the sample stage is disposed at a front focal plane of the first objective lens, the polarized light beam emitted to the PSG is focused on the BFP of the first objective lens via the first lens, and further parallel on the measured sample via the first objective lens, light scattered from the measured sample is collected by the first objective lens and imaged on the BFP thereof, and then on an image acquisition device via the first lens and the PSA.

In a class of the embodiment, the scanning mirror is disposed at the rear of the PSG so that incident light can be vertically emitted to the PSG.

In a class of the embodiment, the device further comprises a beam splitter operating to reflect the polarized light beam, which is then emitted to the first lens.

In a class of the embodiment, the first objective lens operating to collect scattered light is a first objective lens disposed on an optical path in front of the sample stage, and the BFP thereof coincides with the front focal plane of the first lens.

In a class of the embodiment, the device further comprises a second lens disposed on an optical path between the first lens and the PSA, the BFP of the first lens coinciding with the front focal plane of the second lens.

In a class of the embodiment, the device further comprises a second objective lens disposed opposite to the sample stage, and a third lens disposed at the rear thereof, scattered light formed by the polarized light beam emitted to the sample stage transmits the sample and is collected by the second objective lens, and a BFP of the second objective lens coincides with a focal plane of the third lens.

In a class of the embodiment, the device further comprises a fourth lens disposed on an optical path between the third lens and the PSA, a BFP of the third lens coinciding with a front focal plane of the fourth lens.

In a class of the embodiment, the PSG comprises a polarizer, a first compensator and a first servo motor sequentially disposed along an optical path, the polarizer operates to transform an incident light into linear polarized light, the first compensator operates to modulate the linear polarized light into a defined polarization state, and the first servo motor operates to carry the first compensator with a uniform rotation.

In a class of the embodiment, the PSA comprises a second compensator, a second servo motor and a analyzer sequentially disposed along an optical path, the second compensator operates to demodulate the polarized light emitted from sample with a polarization state, the analyzer operates to modulate the demodulated polarization light into linear polarized light, and the second servo motor operates to carry the second compensator with a uniform rotation.

In accordance with another aspect of the invention, provided is method for rapidly measuring a large-area and massive scattered field in nanoscale, comprising steps of:

1) modulating an emitted light beam thereby obtaining a light beam with a polarization state;

2) demodulating an emitted polarized light beam containing information of a measured sample thereby obtaining information of the measured sample;

3) focusing the polarized light beam on a BFP of a first objective lens via a first lens, the first lens and the first objective lens being disposed on an optical path in front of a sample stage, the measured sample on the sample stage being disposed on a front focal plane of the first objective lens, light focused on the BFP of the first objective lens being parallel emitted to the measured sample, light scattered from the measured sample being collected by the first objective lens and imaged on the BFP thereof, and then on an image acquisition device via the first lens and a PSA; and 4) varying an incident angle of the polarized light beam emitted to the lens, a position thereof focused on the BFP of the first objective lens, and thus an angle of a light beam emitted to the sample from the first objective lens, thereby obtaining a scattering distribution image of the measured sample at different incident angles, and enabling rapid and accurate profile measurement of the measured sample in nanoscale by obtaining Mueller matrix at different scattered fields.

In a class of the embodiment, variation of the incident angle is facilitated by a scanning mirror disposed on an optical path in front of or at the rear of the PSG.

In a class of the embodiment, the scanning mirror is disposed at the rear of the PSG so that incident light can be vertically emitted to the PSG.

In a class of the embodiment, the polarized light beam is emitted to the first lens after being reflected by a beam splitter In a class of the embodiment, the first objective lens operating to collect scattered light is a first objective lens disposed on an optical path in front of the sample stage, and the BFP thereof coincides with the front focal plane of the first lens.

In a class of the embodiment, a second lens is disposed on an optical path between the first lens and the PSA, and a BFP of the first lens coincides with a front focal plane of the second lens.

In a class of the embodiment, scattered light formed by the polarized light beam emitted to the sample stage transmits the sample and is collected by a second objective lens disposed opposite to the sample stage, and a BFP of the second objective lens coincides with a focal plane of the third lens.

In a class of the embodiment, a fourth lens is disposed on an optical path between the third lens and the PSA, and a BFP of the third lens coincides with a front focal plane of the fourth lens.

In a class of the embodiment, modulation is facilitated by the PSG, the PSG comprises a polarizer, a first compensator and a first servo motor sequentially disposed along an optical path, the polarizer operates to transform an incident light into linear polarized light, the first compensator operates to modulate the linear polarized light into a light with a defined polarization state, and the first servo motor operates to carry the first compensator with a uniform rotating.

In a class of the embodiment, demodulation is facilitated by the PSA, the PSA comprises a second compensator, a second servo motor and a analyzer sequentially disposed along an optical path, the second compensator operates to demodulate the light with a polarization state, the analyzer operates to modulate the demodulated polarized light into linear polarized light, and the second servo motor operates to carry the second compensator with a uniform rotation.

The device and the method of the invention can rapidly collect the scattered field of the measured sample at multiple incident angles, obtain a 4×4 Mueller matrix (containing sixteen parameters) of the scattered field of the measured sample without changing configuration of a measurement system, and acquire distribution of the scattered field of the measured sample in the BFP of the objective lens.

The device for rapidly measuring a large-area and massive scattered field in nanoscale of the invention is referred to as a Mueller matrix ellipsometry with scatter-field tomography (MEST), and comprises: a laser source operating to provide stable coherent incident light, a scanning mirror operating to change an angle of an incident light beam, a beam expander operating to increase a diameter of the incident light beam to a reasonable value, a polarizer operating to transform the incident light into linear polarized light, a first servo motor operating to load uniform rotation of a first compensator, a first incremental encoder being embedded therein and operating to provide a fixed Z-direction Home signal and servo feedback, an objective lens operating to change an incident angle of the incident light beam, to collect large-angle scattered field of light beam, and to image the distribution of scattered field on a BFP thereof, a measured sample disposed on front focal plane of the objective lens, a lens operating to focus parallel incident light beams on the BFP of the objective lens, and to relay image at emergent light beams, a beam splitter operating to change angles of the incident light beam and the emergent light beam, a second servo motor operating to load uniform rotation of a second compensator, a second incremental encoder being embedded therein and operating to provide a fixed Z-direction Home signal and servo feedback, a analyzer operating to modulate an emergent light beam with polarization state into linear polarized light, an image acquisition device operating to collect and save image information of the scattered field of the measured sample, and a control and data processing system for motion control and data processing of the whole system, comprising a scanning mirror controller operating to control a scanning angel of the scanning mirror, a computer operating to conduct overall system operation and data processing and analyzing, a server motor controller operating to control rotation of two server motors and to receive position signals from two incremental encoders, and a synchronization device operating to capture Z-direction Home signals from two incremental encoders, and to trigger the image acquisition device.

In this invention, the scanning mirror is preferably a dual axial two-dimensional scanning mirror.

In this invention, the first servo motor, the second servo motor and the incremental encoders are of hollow shaft structure or of paraxial hollow shaft structure so that light beams can pass through the center of an optical component loaded thereby. The first incremental encoder and the second incremental encoder each can divide a circle into multiple units separated with an equal angle interval, output position signals that are encoded, and generate a Z-direction Home signal every time it rotates one circle.

In this invention, the first compensator and the second compensator are optical anisotropic components that can generate phase delay retardance in two directions vertical to each other, comprising mica wave plates, quartz wave plates, liquid crystal wave plates, $MgF_2$ wave plates, or Fresnel prisms.

In this invention, the polarizer and the analyzer are polarizing components which can transform arbitrary state of polarized light into linear polarized light, comprising dichroism linear polarizers, Glan Taylor polarizing prisms, and Glan Thompson polarizing prisms.

In this invention, the beam splitter has no effect on measuring a polarization state of a light beam, and a splitting ratio thereof is 0.5/0.5.

In this invention, the objective lens is an infinite optical design Plan Apochromatic objective lens (Strain-Free) objective lens, or a Plan Semi Apochromatic (Strain-Free) objective lens.

In this invention, the image acquisition device is a charge coupled device (CCD) or a complementary metal oxide semiconductor (CMOS) image sensor.

In this invention, the synchronization device mainly operates to determine an instantaneous position of an optical axis of the compensator at initial time when the image acquisition device collects an image. Correct results can be obtained only if an image collected by the image acquisition device corresponds to the optical axis of each of the compensators, as the compensators are always in a motion state during measurement. The two compensators are respectively loaded by two servo motors, and a rotation speed of each of the servo motors is constant during measurement. Therefore, once the instantaneous position of the optical axis of the compensator at initial time when the image acquisition device collects an image is determined, the position of the optical axis of the compensator at any time can be determined.

A measurement method using the above-mentioned device for rapidly measuring a large-area and massive scattered field in nanoscale comprises steps of:

1. initializing a hardware system of the MEST;
2. rotating the scanning mirror to a preset position, and starting the synchronization device via a computer;
3. exposing the image acquisition device at preset integration time, and transforming and saving a collected image;
4. repeating steps 2 and 3 until the scanning mirror finishes rotating at all preset positions; and
5. collecting intensity of every pixel point in the image collected by the image acquisition device, calculating sixteen elements of a Mueller matrix, and obtaining distribution of a scattered field of a measured sample by calculating an image at multiple incident angles.

Further, step 1 comprises:

(1) starting a laser source and waiting until a stable output;
(2) loading the first rotating compensator and the second rotating compensator by the first servo motor and the second servo motor respectively, controlling the first servo motor and the second servo motor to uniformly rotate at a speed ratio of p:q via a servo controller by the computer, and transmitting a pulse signal to a scanning mirror controller by a server motor controller after the servo motors operate stably;
(3) starting the image acquisition device, setting an exposure time t and the number of images Q that need to be collected during measurement, and enabling the image acquisition device to be in an external trigger mode; where Q=N×L, N represents the times of sampling in an optical cycle, and L represents the number of repeated sampling cycles;

Further, step (2) comprises:

(2-1) the computer controls the first servo motor and the second servo motor to return to respective Home position via the servo motor controller;
(2-2) the computer controls the first servo motor and the second servo motor to synchronously start via the servo motor controller, and enables the first servo motor and the second servo motor to uniformly rotate at rotation speed of $p*\omega$ and $q*\omega$ respectively, where $\omega$ represents a base frequency of each of the first servo motor and the second servo motor;
(2-3) the incremental encoder of each of the first servo motor and the second servo motor transmits a Z-direction Home signal every time, when the first servo motor or the second servo motor rotate to the Home position;
(2-4) the servo motor controller transmits a pulse signal to the scanning mirror controller after the first servo motor and the second servo motor operate stably.

Further, step 3 comprises:

(4) starting the synchronization device to capture the Z-direction Home signal of each of the first servo motor and the second servo motor;
(5) transmitting a trigger pulse signal to the image acquisition device by the synchronization device after simultaneously capturing the Z-direction Home signal of each of the first servo motor and the second servo motor;
(6) sampling Q images at the preset integration time t by the acquisition device after receiving the trigger pulse signal, and saving the images into the computer.

To summarize, the present invention has following advantages over the prior art:

Firstly, by using the scanning mirror to change an incident angle of an incident light beam, and thus a position thereof on the BFP of the objective lens, it is possible to illuminate sample at multiple incident angles;

Secondly, by using a large-numerical-aperture objective lens to collect the scattered field, and imaging Fourier spatial images of the objective lens on the image acquisition device via the imaging lens without obtaining actual images of the measured sample, it is possible to overcome a problem with a conventional optical scattering device that only information of a single scattered field (namely zeroth-order diffraction light) can be obtained, and to represent distribution of the scattered field;

Thirdly, by using the ellipsometry for measurement, only variation information regarding the polarization state of the scattered field, instead of an absolute amplitude and an absolute phase thereof, is obtained, which prevents introduction of a complex non-common optical path, and enables simpler implementation and calibration of the MEST;

Fourthly, the MEST is capable of obtaining 16 elements of the Mueller matrix of the measured sample by one measurement, distribution of the Mueller matrix that represents optical property and the scattered field of the measured sample, thus three-dimensional profile parameters of the measured sample are obtained by using distribution of the Mueller matrix at different incident angles.

DETAILED DESCRIPTION OF THE EMBODIMENTS

For clear understanding of the objectives, features and advantages of the invention, detailed description of the invention will be given below in conjunction with accompanying drawings and specific embodiments. It should be noted that the embodiments are only meant to explain the invention, and not to limit the scope of the invention.

Figure 1:
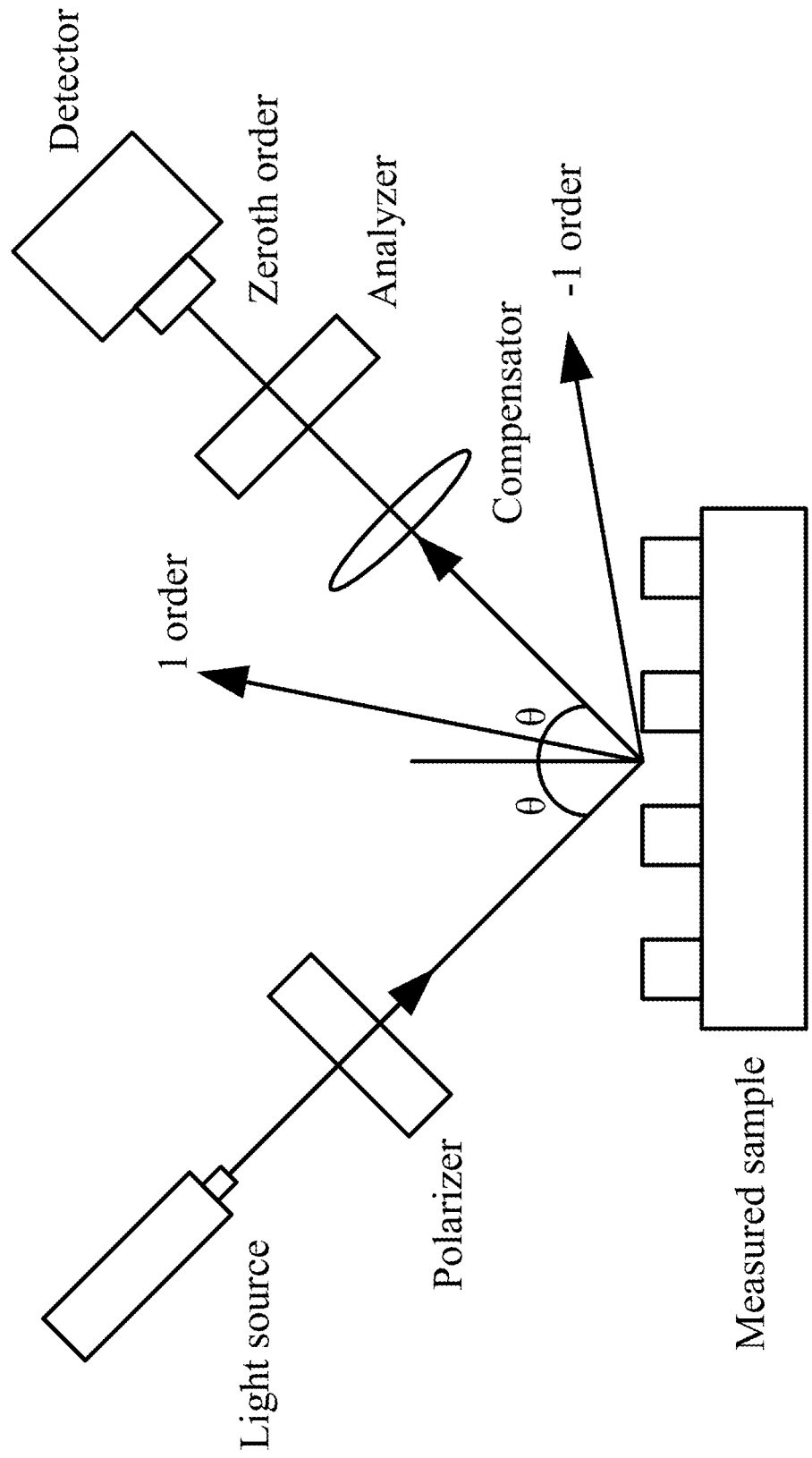
FIG. 1 is a schematic view of a conventional optical scatterometer.
Figure 2:
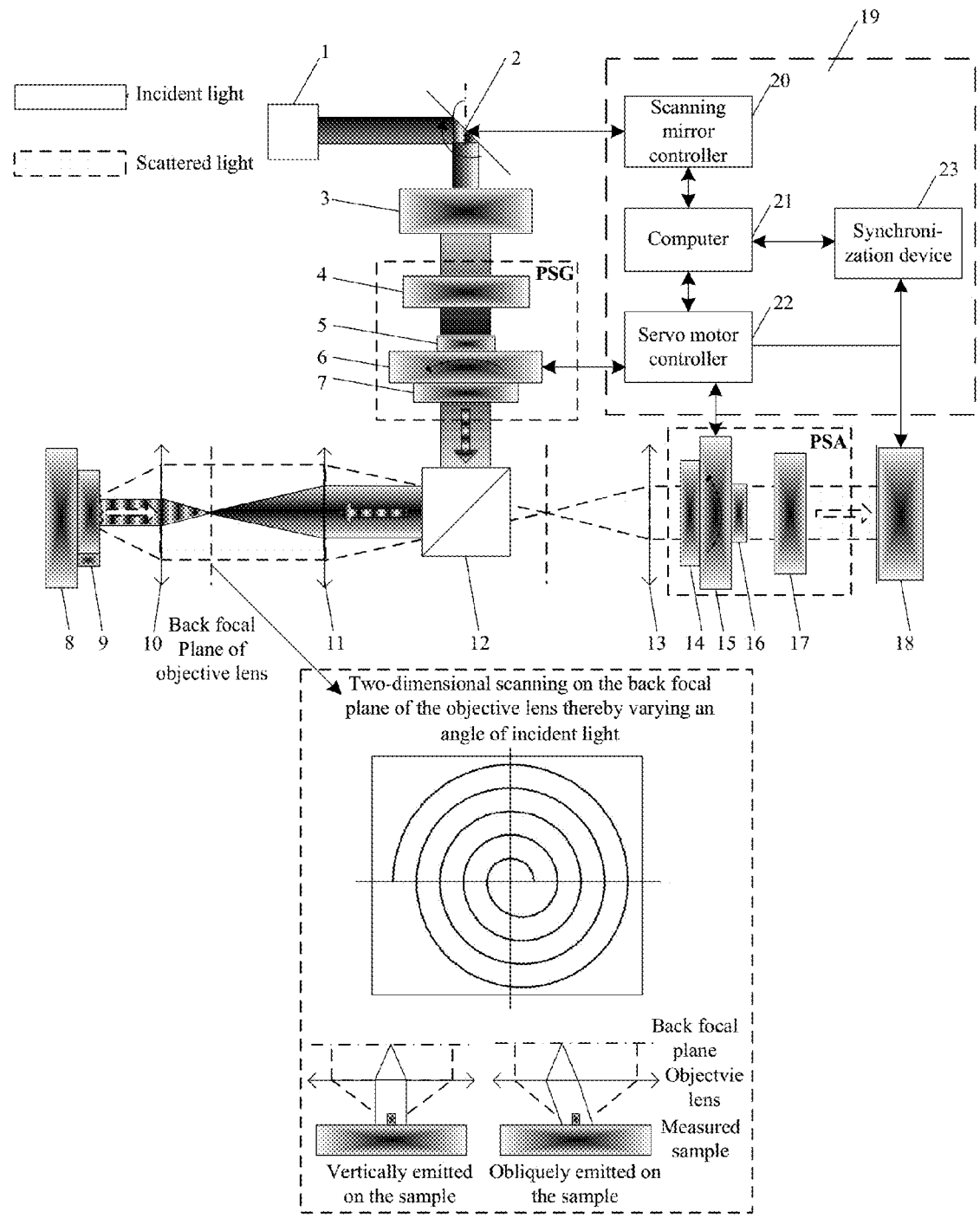
FIG. 2 is a schematic view of a reflecting Mueller matrix ellipsometry with scatter-field tomography of an exemplary embodiment of the invention.

As shown in FIG. 2, a reflecting scattered Mueller matrix ellipsometry with scatter-field tomography in accordance with a first embodiment of the invention comprises a laser source 1, a scanning mirror 2, a beam expander 3, a polarizer 4, a first incremental encoder 5, a first servo motor 6, a first compensator 7, a sample stage 8, a sample 9, an objective lens 10, a first lens 11, a beam splitter 12, a second lens 13, a second compensator 14, a second servo motor 15, a second incremental encoder 16, a analyzer 17, an image acquisition device 18, and a control and data processing device 19.

The laser source 1 operates to provide stable coherent incident light.

The scanning mirror 2 operates to change an angle of an incident light beam, and is preferably a two-dimensional scanning mirror.

The beam expander 3 operates to increase a diameter of the incident light beam to a reasonable value, and does not change a transmission direction of the light beam. The beam expander 3 is variable magnification and focus, and can be a sliding lens or a rotary lens.

The polarizer 4 operates to transform the incident light into linear polarized light, and can be a polarizing component capable of transforming arbitrary polarized light into linear polarized light, and is preferably a dichroism linear polarizer, a Glan Taylor polarizing prism, and a Glan Thompson polarizing prism.

The first servo motor 6 operates to load uniform rotation of the first compensator 7, the first incremental encoder 5 being embedded therein and operating to provide a fixed Z-direction Home signal and servo feedback. The first servo motor 6 and the first incremental encoder 5 embedded therein are of hollow shaft structure or of paraxial hollow shaft structure so that light beams can pass through the center of an optical component loaded thereby.

The first incremental encoder 5 can divide a circle into multiple units separated with an equal angle interval, output position signals that are encoded, and generate a Z-direction Home signal every time it rotates one circle. The first compensator 7 is an optical anisotropic component that can generate phase delay retardance in two directions vertical to each other, preferably a mica wave plate, a quartz wave plate, a liquid crystal wave plate, a $MgF_2$ wave plate, or a Fresnel prism.

The beam expander 3, the polarizer 4, and the first compensator 7 are disposed on a common optical axis.

The sample stage 8 is a rotary table that can rotate at 360°. The measured sample 9 is disposed on the sample stage 8, and on a front focal plane of the objective lens 10.

The objective lens 10 operates to change an incident angle of the incident light beam with the scanning mirror 2 thereby measuring the measured sample at multiple incident angles, to collect large-angle scattered field of emergent light beam, and to distribute and image the scattered field on a BFP thereof. In this embodiment, the objective lens 10 can be an infinite optical design Plan Apochromatic (Strain-Free) objective lens or a Smi Apochromatic (Strain-Free) objective lens that should be suitable for a band of the laser source 1.

The first lens 11 operates to focus parallel incident light beams on the BFP of the objective lens 10, and to relay image at emergent light beams. In this embodiment, the first lens 11 can be an achromatic lens operating at a wide band, or at a single band corresponding to the band of the laser source 1. A dashed part in FIG. 2 illustrates a process of scanning light beams on the BFP of the objective lens 10 thereby measuring the measured sample at different incident angles. Light beams scanned by the scanning mirrors 2 are sequentially emitted on the first lens 11 at different angles. As the light beams are vertically emitted on the first lens 11, the light beams are focus on a center point of the BFP of the objective lens 10, and then on the measured sample 9 via the objective lens 10. As the light beams are obliquely emitted on the first lens 11, a focus point of the light beams is to deviate from the center point of the BFP of the objective lens 10, and then the light beams are emitted on the measured sample 9 at an incident angle via the objective lens 10.

The beam splitter 12 operates to change angles of the incident light beam and the emergent light beam. The beam splitter 12 has no effect on measuring a polarization state of a light beam, and a splitting ratio thereof is 0.5/0.5.

The second lens 13 operates to relay image the scattered field on BFP of the objective lens 10. In this embodiment, the second lens 13 can be an achromatic lens operating at a wide band, or at a single band corresponding to the band of the laser source 1.

The second servo motor 15 operates to load uniform rotation of the second compensator 14, the second incremental encoder 16 being embedded therein and operating to provide a fixed Z-direction Home signal and servo feedback. The second servo motor 15 and the second incremental encoder 16 embedded therein are of hollow shaft structure or of paraxial hollow shaft structure so that light beams can pass through the center of an optical component loaded thereby.

The second incremental encoder 16 can divide a circle into multiple units separated with an equal angle interval, output position signals that are encoded, and generate a Z-direction Home signal every time it rotates one circle. The second compensator 14 is an optical anisotropic component that can generate a phase delay retardance in two directions vertical to each other, comprising a mica wave plate, a quartz wave plate, a liquid crystal wave plate, a $MgF_2$ wave plate, or a Fresnel prism.

The analyzer 17 operates to modulate polarization state of emergent light into linear polarized light, and can be a polarizing component capable of transforming arbitrary polarized light into linear polarized light, comprising a dichroism linear polarizer, a Glan Taylor polarizing prism, or a Glan Thompson polarizing prism.

The image acquisition device 18 operates to collect and save image information of the scattered field of the measured sample 9. In this embodiment, the image acquisition device 18 is preferably a charge coupled device (CCD) or a complementary metal oxide semiconductor (CMOS) image sensor with an external trigger function.

The objective lens 10, the first lens 11, the beam splitter 12, the second compensator 14, the second lens 13, the analyzer 17 and the image acquisition device 18 are disposed on a common optical axis.

The control and data processing device 19 operates for motion control and data processing of the whole MEST, and comprise a scanning mirror controller 20 operating to control a scanning angle of the scanning mirror 2, a computer 21 operating to control the whole MEST and to process and analyze data, a servo motor controller 22 operating to control rotation of the first servo motor 6 and the second servo motor 15 and to receive position signals from the first incremental encoder 5 and the second incremental encoder 16, and a synchronization device 23 operating to capture Z-direction Home signals from the first incremental encoder 5 and the second incremental encoder 16, and to trigger the image acquisition device 18.

Figure 3:
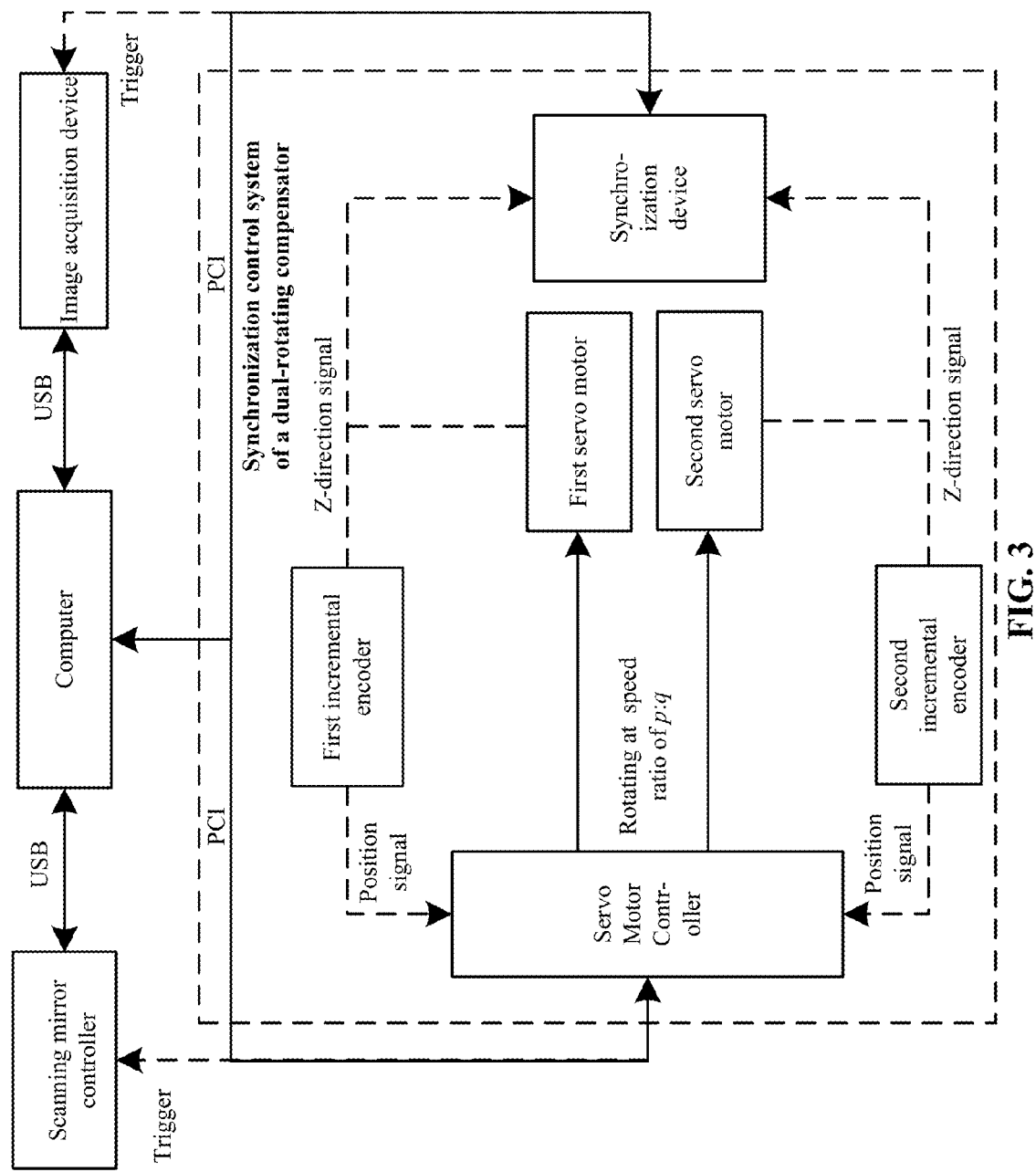
FIG. 3 is a block diagram of a control and data processing system of Mueller matrix ellipsometry with scatter-field tomography of the invention.

As shown in FIG. 3, the control and data processing system of the MEST comprises the computer, the scanning mirror controller, the servo motor controller, the synchronization device, the first servo motor, the first incremental encoder, the second servo motor, the second incremental encoder, and the image acquisition device. The computer is electrically connected to the scanning mirror controller and the image acquisition device via USB standard interfaces, and to the servo motor controller and the synchronization device via PCI interfaces. The servo motor controller is electrically connected to the first servo motor, the second servo motor, the first incremental encoder, and the second incremental encoder, receives motion control instructions from the computer thereby controlling the first servo motor and the second servo motor to return to the Home position and to uniformly rotate at a speed ratio of p:q, and conducts close-loop control according to feedback signals from the first incremental encoder and the second incremental encoder, which ensures precision and stability of motion. The scanning mirror controller is electrically connected to the scanning mirror, and drives and controls the scanning mirror to move to a preset position according to instructions from the computer. The synchronization device is electrically connected to the first incremental encoder, the second incremental encoder and the image acquisition device, and transmits a trigger pulse signal to the image acquisition device upon receiving the Z-direction Home signals from the first incremental encoder and the second incremental encoder. After receiving the trigger pulse signal, the image acquisition device collects images according to preset parameters.

Figure 4:
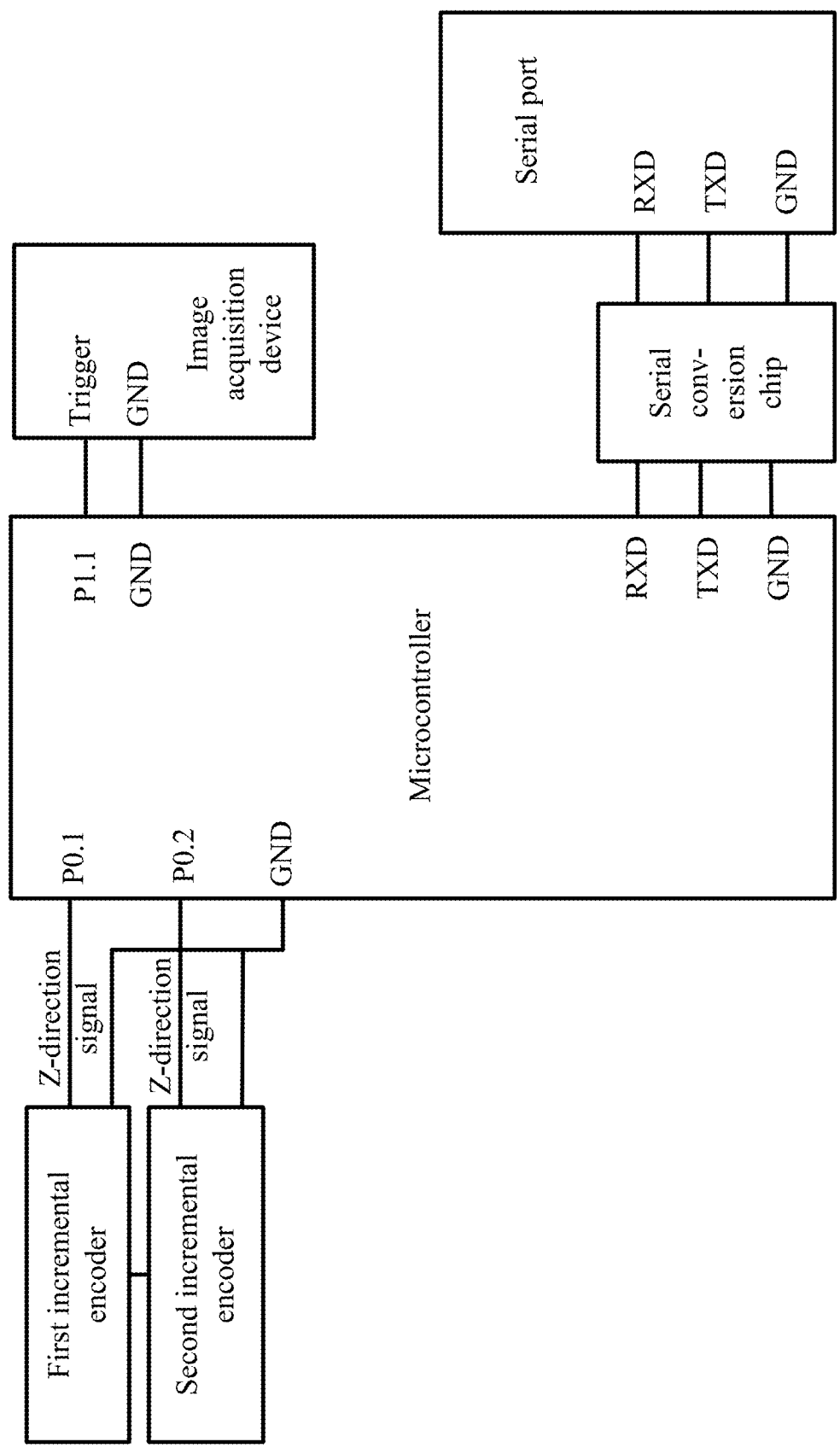
FIG. 4 illustrates connection between a synchronization device of the invention and external hardware.

FIG. 4 illustrates connection between the synchronization device (shown as a microcontroller) and external hardware. Firstly, Z-direction Home signal lines and ground wires of the first incremental encoder and the second incremental encoder are led out; secondly, the Z-direction Home signal line and the ground wire of the first incremental encoder are respectively connected to a pin P0.1 and a pin GND of the microcontroller; thirdly, the Z-direction Home signal line and the ground wire of the second incremental encoder are respectively connected to a pin P0.2 and the pin GND of the microcontroller; fourthly, a pin P1.1 and the pin GND of the microcontroller are respectively connected to a pin Trigger and a pin GND of the image acquisition device; fifthly, pins RXD, TXD and GND of the microcontroller are connected to a standard serial port of the computer via serial ports. It should be noted that the above-mentioned connection is exemplary connection of the microcontroller only (where pins P0.1 and P0.2 are used as input ends, and pin P1.1 is used as a pulse output end), and other appropriate ways of connection can also be used.

Figure 5:
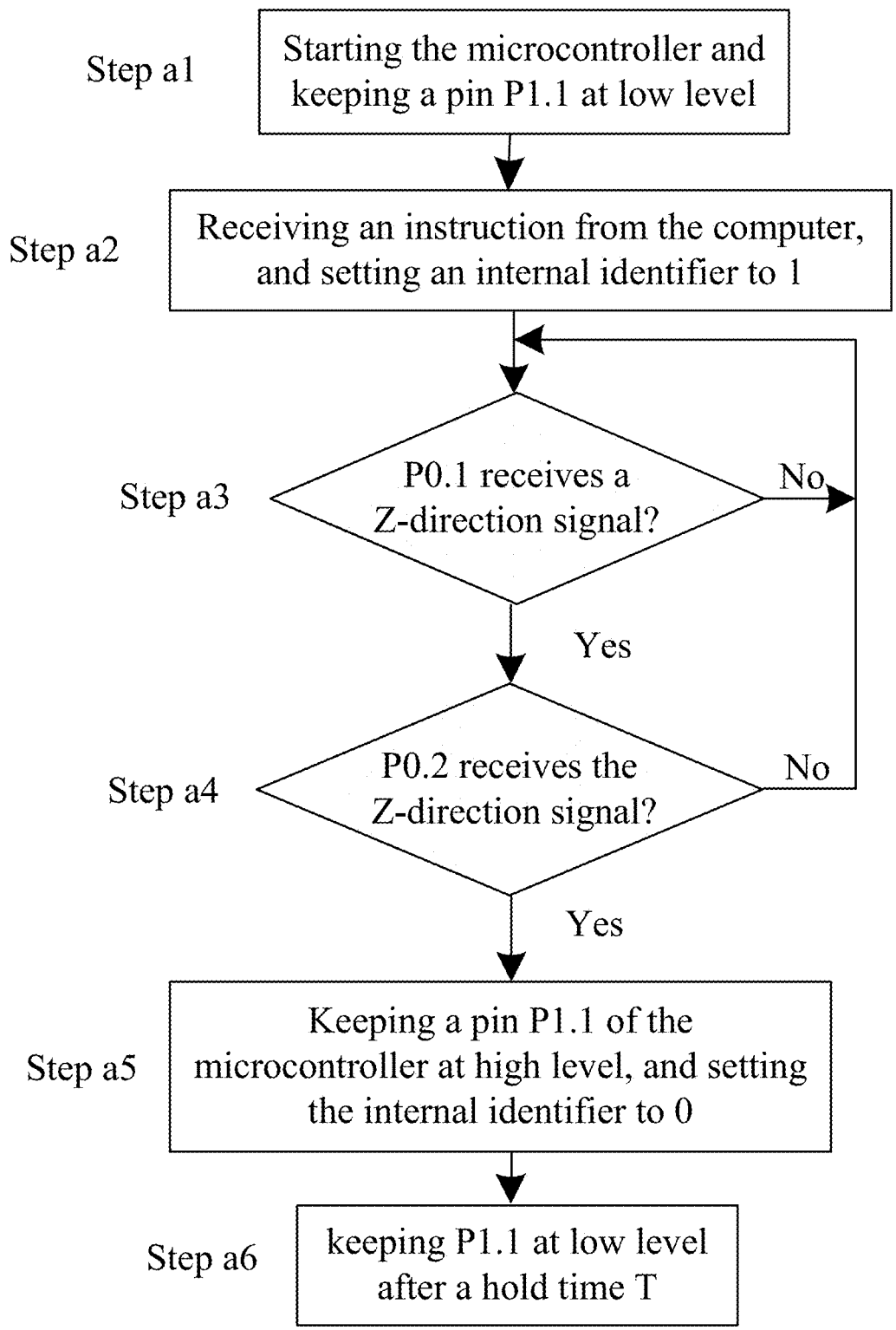
FIG. 5 is a flowchart illustrating operation of the synchronization device of the invention.

To measure distribution of a scattered field of a sample, such as a fin field-effect transistor (FinFET), a measurement method using MEST of a first embodiment of the invention comprises steps of:

1. initializing a hardware system of the MEST, comprising:

(1) installing and debugging all optical components, and ensuring all hardware devices are in proper connection and system software is successfully run;

(2) starting the laser source 1 and waiting until a stable output;

(3) loading the first compensator 7 and the second compensator 14 by the first servo motor 6 and the second servo motor 15 respectively, controlling the first servo motor 6 and the second servo motor 15 to uniformly rotate at a speed ratio of p:q via a servo controller by the computer, and transmitting a pulse signal to the scanning mirror controller by a server motor controller after the first servo motor 6 and the second servo motor 15 operate stably;

(4) starting the image acquisition device 18, setting an exposure time t and the number of images Q that need to be collected during measurement, and enabling the image acquisition device 18 to be in an external trigger mode; where Q=N×L, N represents the times of sampling in an optical cycle, and L represents the number of repeated sampling cycles; this step comprises sub steps of (4-1) the computer controls the first servo motor and the second servo motor to return to respective Home location via the servo motor controller;

(4-2) the computer controls the first servo motor and the second servo motor to synchronously start via the servo motor controller, and enables the first servo motor and the second servo motor to uniformly rotate at rotation speed of p*ω and q*ω respectively, where ω represents a base frequency of each of the first servo motor and the second servo motor;

(4-3) the incremental encoder of each of the first servo motor and the second servo motor transmit a Z-direction Home signal every time the first servo motor or the second servo motor rotate to the Home position;

(4-4) the servo motor controller transmits a pulse signal to the scanning mirror controller after the first servo motor and the second servo motor operate stably;

2. rotating the scanning mirror 2 to a preset position, and starting the microcontroller via the computer; specifically, the microcontroller performs the following seven steps as shown in FIG. 5:

(a1) starting the microcontroller and keeping a pin P1.1 thereof at low level;

(a2) receiving an instruction from the computer by the microcontroller, setting an internal identifier to 1, and enabling pins P0.1 and P0.2 thereof to capture Z-direction Home signals from the first incremental encoder and the second incremental encoder;

(a3) detecting whether the pin P0.1 of the microcontroller receives the Z-direction Home signal from the first incremental encoder, continuing to capture the signal if not, and proceeding to step (a4) if yes;

(a4) detecting whether the pin P0.2 of the microcontroller receives the Z-direction signal from the second incremental encoder, returning to step (a3) if not, and proceeding to step (a5) if yes;

(a5) keeping the pin P1.1 of the microcontroller at high level, and setting the internal identifier to 0;

(a6) setting the pin P1.1 of the microcontroller to low level after time T, T corresponds to hold time of least high level of the image acquisition device, and specifically, time T should be greater than the hold time of least high level of the image acquisition device;

High level and low level in above steps are TTL level signals. Under a room temperature, output high level is 3.5 V, output low level is 0.2 V. As for the least high level and low level, input high level>=2.0 V, input low level<=0.8 V, and a noise margin is 0.4 V.

3. receiving the trigger pulse signal from the microcontroller, exposing the at preset integration time, and transforming and saving a collected image by the image acquisition device;

4. repeating steps 2 and 3 until the scanning mirror finishes rotating at all preset positions; and 5. collecting intensity of every pixel point in the image collected by the image acquisition device, calculating sixteen elements of a Mueller matrix, and obtaining distribution of a scattered field of a measured sample by calculating an image at multiple incident angles.

A measurement method using the MEST of a second embodiment of the invention comprises steps of:

1. initializing a hardware system of the MEST, comprising:

(1) starting the laser source 1 and waiting until a stable output;

(2) loading the first compensator and the second compensator by the first servo motor and the second servo motor respectively, controlling the first servo motor and the second servo motor to uniformly rotate at a speed ratio of p:q via a servo controller by the computer, and transmitting a pulse signal to a scanning mirror controller by a server motor controller after the servo motors operate stably;

(3) starting the image acquisition device, setting an exposure time t and the number of images Q that need to be collected during measurement, and enabling the image acquisition device to be in an external trigger mode; where Q=N×L, N represents the times of sampling in an optical cycle, and L represents the number of repeated sampling cycles;

step (3) comprises sub-steps of:

(3-1) the computer controls the first servo motor and the second servo motor to return to respective Home location via the servo motor controller;

(3-2) the computer controls the first servo motor and the second servo motor to synchronously start via the servo motor controller, and enables the first servo motor and the second servo motor to uniformly rotate at rotation speed of $p*\omega$ and $q*\omega$ respectively, where $\omega$ represents a base frequency of each of the first servo motor and the second servo motor;

(3-3) the incremental encoder of each of the first servo motor and the second servo motor transmit a Z-direction Home signal every time the first servo motor or the second servo motor rotate to the Home position;

(3-4) the servo motor controller transmits a pulse signal to the scanning mirror controller after the first servo motor and the second servo motor operate stably;

2. rotating the scanning mirror to a preset position, and starting the synchronization device via a computer;

3. exposing the image acquisition device at preset integration time, and transforming and saving a collected image; this step comprises sub-steps of:

(4) starting the synchronization device to capture the Z-direction Home signal of each of the first servo motor and the second servo motor;

(5) transmitting a trigger pulse signal to the image acquisition device by the synchronization device after capturing the Z-direction Home signal of each of the first servo motor and the second servo motor;

(6) sampling Q images at the preset integration time t by the acquisition device after receiving the trigger pulse signal, and saving the images into the computer;

4. repeating steps 2 and 3 until the scanning mirror finishes rotating at all preset positions; and 5. collecting intensity of every pixel point in the image collected by the image acquisition device, calculating sixteen elements of a Mueller matrix, and obtaining distribution of a scattered field of a measured sample by calculating an image at multiple incident angles. This step comprises sub-steps of:

(6.1) establishing a system measurement model represented as the following linear equation:

$$I_q = A_q^T M S_q = \sum_{j=0}^{3} \sum_{k=0}^{3} a_{q,j} m_{j,k} s_{q,k} = \sum_{j=0}^{3} \sum_{k=0}^{3} w_{q,j,k} m_{j,k} \quad (1)$$

in which:

$$A_q = (a_{q,0} \quad a_{q,1} \quad a_{q,2} \quad a_{q,3}) \quad (2)$$

$$M = \begin{pmatrix} m_{0,0} & m_{0,1} & m_{0,2} & m_{0,3} \\ m_{1,0} & m_{1,1} & m_{1,2} & m_{1,3} \\ m_{2,0} & m_{2,1} & m_{2,2} & m_{2,3} \\ m_{3,0} & m_{3,1} & m_{3,2} & m_{3,3} \end{pmatrix} \quad (3)$$

$$S_q = \begin{pmatrix} s_{q,0} \\ s_{q,1} \\ s_{q,2} \\ s_{q,3} \end{pmatrix} \quad (4)$$

$$w_{q,j,k} = a_{q,j} s_{q,k} \quad (5)$$

where $I_q$ represents a light intensity signal of a pixel of the image acquisition device, $A_q$ represents a PSA vector, $S_q$ represents a PSG vector, $q=0, 1, \ldots, Q-1$ represents the $q^{th}$ measurement component of the MEST, Q represents the number of measurement, namely the number of images that need to be collected by the image acquisition device, M represents a Mueller matrix of the measured sample, and an element thereof is denoted by $m_{j,k}$, $a_{q,j}$ and $S_{q,k}$ respectively corresponds to an element in vectors $A_q$ and $S_q$, $w_{q,j,k}$ represents a coefficient of the $q^{th}$ measurement component $I_q$ with respect to the element $m_{j,k}$ in the $j^{th}$ row and the $k^{th}$ column, which indicates transfer characteristics of the MEST, and $j=0, 1, 2, 3$ and $k=0, 1, 2, 3$ respectively represents a serial number of an element in the corresponding vector.

(6.2) substituting the Mueller matrix M of the measured sample with a 16×1 column vector $\vec{M}$, and then $$I_q = W_q \times \vec{M} = (a_{q,0}s_{q,0} \ a_{q,0}s_{q,1} \ \ldots \ a_{q,3}s_{q,3}) \times \begin{pmatrix} m_{0,0} \\ m_{0,1} \\ \vdots \\ m_{3,3} \end{pmatrix} \quad (6)$$

All Q times of measurement can be denoted by a Q×16 system matrix W, where $W_q$ represents the $q^{th}$ row of the matrix W. The $Q^{th}$ measurement result is represented by a measurement vector I in the following equation (7), where $I_q$ represents the $q^{th}$ row of the vector I. After solving equation (7), it is possible to obtain sixteen elements of a Mueller matrix of one pixel point of the measured sample, and elements of a Mueller matrix of a region corresponding to the measured sample.

$$I = W \times \vec{M} = \begin{pmatrix} I_0 \\ I_1 \\ \vdots \\ I_{Q-1} \end{pmatrix} = \begin{pmatrix} w_{0,0,0} & w_{0,0,1} & \ldots & w_{0,3,3} \\ w_{1,0,0} & w_{1,0,1} & \ldots & w_{1,3,3} \\ \vdots & \vdots & & \vdots \\ w_{Q-1,0,0} & w_{Q-1,0,1} & \ldots & w_{Q-1,3,3} \end{pmatrix} \times \begin{pmatrix} m_{0,0} \\ m_{0,1} \\ \vdots \\ m_{3,3} \end{pmatrix} \quad (7)$$

Figure 6:
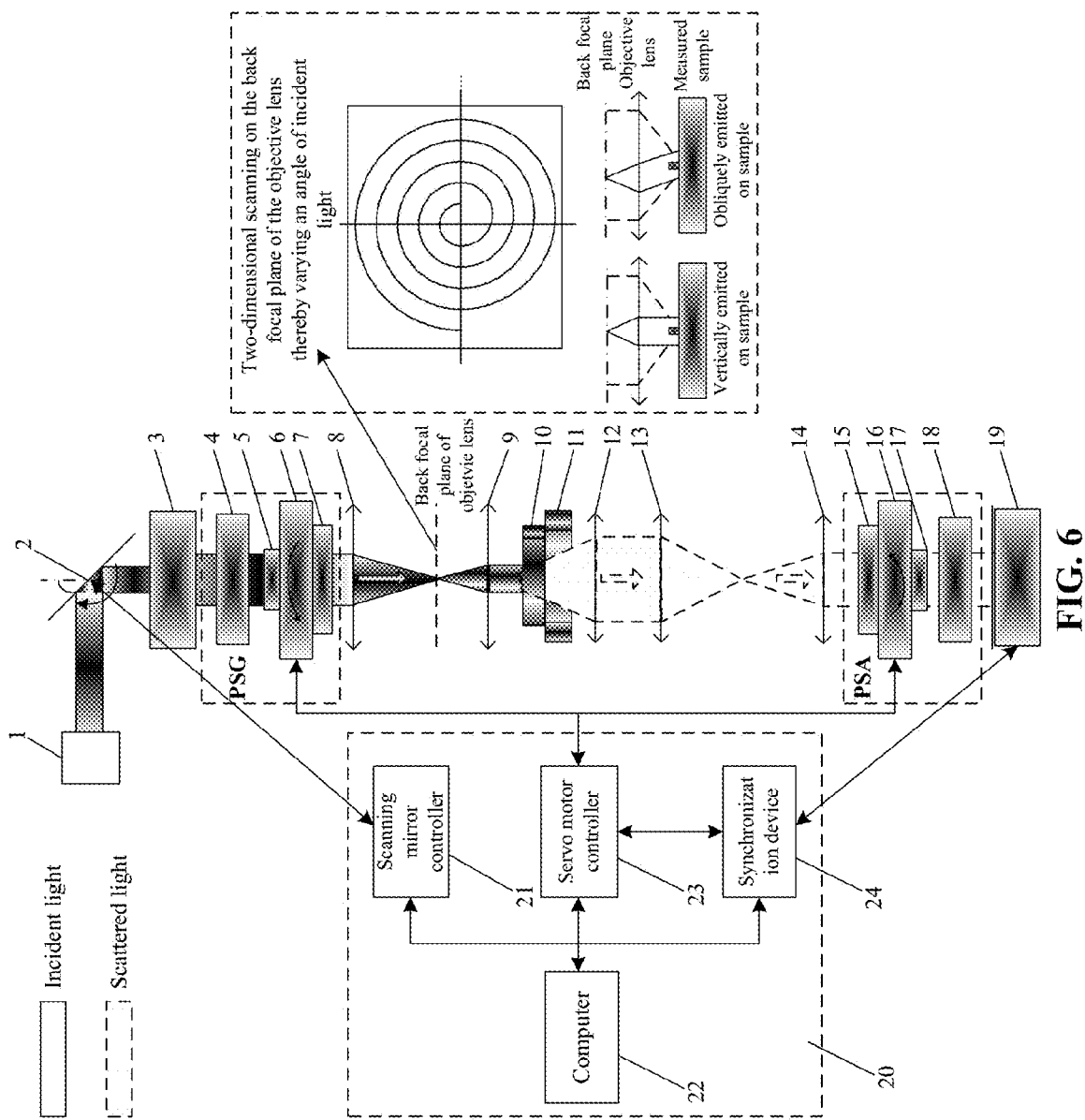
FIG. 6 is a schematic view of a transmission scattered Mueller matrix ellipsometry with scatter-field tomography of another exemplary embodiment of the invention.

As shown in FIG. 6, a transmission MEST of an embodiment of the invention comprises a laser source 1, a scanning mirror 2, a beam expander 3, a polarizer 4, a first incremental encoder 5, a first servo motor 6, a first compensator 7, a first lens 8, an first objective lens 9, a sample 10, a sample stage 11, an second objective lens 12, a second lens 13, a third lens 14, a second compensator 15, a second servo motor 16, a second incremental encoder 17, a analyzer 18, an image acquisition device 19, and a control and data processing device 20.

The laser source 1 operates to provide stable coherent incident light.

The scanning mirror 2 operates to change an angle of an incident light beam, and is preferably a two-dimensional scanning mirror.

The beam expander 3 operates to increase a diameter of the incident light beam to a reasonable value, and does not change a transmission direction of the light beam. The beam expander 3 is variable magnification and focus, and can be a sliding lens or a rotary lens. The polarizer 4 operates to transform the incident light beam into linear polarized light, and can be a polarizing component capable of transforming arbitrary polarized light into linear polarized light, and is preferably a dichroism linear polarizer, a Glan Taylor polarizing prism, and a Glan Thompson polarizing prism.

The first servo motor 6 operates to load uniform rotation of the first compensator 7, the first incremental encoder 5 being embedded therein and operating to provide a fixed Z-direction Home signal and servo feedback. The first servo motor 6 and the first incremental encoder 5 embedded therein are of hollow shaft structure or of paraxial hollow shaft structure so that light beams can pass through the center of an optical component loaded thereby.

The first incremental encoder 5 can divide a circle into multiple units separated with an equal angle interval, output position signals that are encoded, and generate a Z-direction Home signal every time it rotates one circle. The first compensator 7 is an optical anisotropic component that can generate a phase delay retardance in two directions vertical to each other, preferably a mica wave plate, a quartz wave plate, a liquid crystal wave plate, a $MgF_2$ wave plate, or a Fresnel prism.

The first lens 8 operates to focus parallel incident light beams on the BFP of the first objective lens 9, and a distance between the first lens 8 and the BFP of the first objective lens 9 is a focal length thereof. The first lens 8 is preferably an achromatic lens operating at a wide band, or at a single band corresponding to the band of the laser source 1.

An angle of an emergent light beam from the first objective lens 9 varies along with a position of a focus spot on the BFP, and thus measurement of the measured sample at multiple incident angles is facilitated. The first objective lens 9 can be an infinite optical design Plan Apochromatic (Strain-Free) objective lens or a Smi Apochromatic (Strain-Free) objective lens that must be suitable for a band of the laser source 1.

The sample stage 11 is a rotary table that can rotate at 360°. The measured sample 10 is disposed on the sample stage 11, and on a front focal plane of the first objective lens 9.

The second objective lens 12 operates to collect a large-angle scattered field of the measured sample, and to image the scattered field on a BFP thereof. The second objective lens 12 can be an infinite optical design Plan Apochromatic (Strain-Free) objective lens or a Smi Apochromatic (Strain-Free) objective lens that must be suitable for the band of the laser source 1.

The second lens 13 operates for relay imaging, and a distance between the second lens 13 and the BFP of the second objective lens 12 is a focal length thereof. The second lens 13 can be an achromatic lens operating at a wide band, or at a single band corresponding to the band of the laser source 1.

The third lens 14 operates for relay imaging, and a focal length thereof must be equal to a distance between it and an image sensitive element of the image acquisition device. The third lens 14 can be an achromatic lens operating at a wide band, or at a single band corresponding to the band of the laser source 1.

The second servo motor 16 operates to load uniform rotation of the second compensator 15, the second incremental encoder 17 being embedded therein and operating to provide a fixed Z-direction Home signal and servo feedback. The second servo motor 16 and the second incremental encoder 17 embedded therein are of hollow shaft structure or of paraxial hollow shaft structure so that light beams can pass through the center of an optical component loaded thereby. The second incremental encoder 17 can divide a circle into multiple units separated with an equal angle interval, output position signals that are encoded, and generate a Z-direction Home signal every time it rotates one circle. The second compensator 15 is an optical anisotropic component that can generate a phase delay retardance in two directions vertical to each other, comprising a mica wave plate, a quartz wave plate, a liquid crystal wave plate, a $MgF_2$ wave plate, or a Fresnel prism.

The analyzer 18 operates to modulate the demodulated polarized light into linear polarized light, and can be a polarizing component capable of transforming arbitrary polarized light into linear polarized light, comprising a dichroism linear polarizer, a Glan Taylor polarizing prism, or a Glan Thompson polarizing prism.

The image acquisition device 19 operates to collect and save image information of the scattered field of the measured sample 10. In this embodiment, the image acquisition device 19 is preferably a charge coupled device (CCD) or a complementary metal oxide semiconductor (CMOS) image sensor with an external trigger function.

The beam expander 3, the polarizer 4, the first compensator 5, the first lens 8, the first objective lens 9, the second objective lens 12, the second lens 13, the third lens 14, the second compensator 15, the analyzer 18, and the image acquisition device 19 are disposed on a common optical axis.

The control and data processing device 20 operates for motion control and data processing of the whole MEST, and comprises a scanning mirror controller 21 operating to control a scanning angle of the scanning mirror 2, a computer 22 operating to control the whole MEST and to process and analyze data, a servo motor controller 23 operating to control rotation of the first servo motor 6 and the second servo motor 16 and to receive position signals from the first incremental encoder 5 and the second incremental encoder 17, and a synchronization device 24 operating to capture Z-direction Home signals from the first incremental encoder 5 and the second incremental encoder 17, and to trigger the image acquisition device 19.

To measure distribution of a scattered field of a sample, such as a fin field-effect transistor (FinFET), a measurement method using the MEST is almost the same as that described with respect to the first embodiment, and a control and data processing system, connection of the synchronization device, and a flowchart of the synchronization device of the MEST are the same as those in the first embodiment.

The present invention called MEST is based on an optical scattering device of a conventional ellipsometry, along with the optical diffraction tomography technology. The present invention employs a large-numerical-aperture objective lens and a scanning mirror to facilitate rapidly two-dimensional scanning of light beams on a BFP of the objective lens, which enables the MEST to be able to rapidly collect information of the scattered field of the measured sample at multiple incident angles, and overcomes a problem with a conventional ellipsometry that it can only obtain information of a single scattered field (namely zeroth-order diffraction light). Compared with a conventional optical diffraction tomography technology, the MEST obtains information regarding variation of the polarization state of the scattered field, instead of an absolute amplitude and an absolute phase thereof, which prevents introduction of a complex non-common optical path, and enables simpler implementation and calibration of the MEST. Moreover, variation information of the polarization state of each scattered field are obtained by introducing the Mueller matrix ellipsometry into the invention contains a 4×4 Mueller matrix (16 elements), which enables the invention to obtain richer measurement information than a conventional optical scattering device, and makes it possible to facilitate more sensitive and complete three-dimensional profile measurement in nanoscale. Meanwhile, the MEST is essentially a remote-field optical measurement method that can meet requirement of nanometer measurement for rapidness, low cost, and nondestructive property, and is easy for operation and full-automatic and integral measurement.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for measuring a large-area and massive scattered field, the device comprising:
    (a) a polarization state generator being disposed on an output optical path of a laser source, and operating to modulate a light beam emitted thereon thereby obtaining a light beam with a polarization state;
    (b) a polarization state analyzer operating to demodulate a polarized light beam emitted thereon and containing information of a measured sample thereby obtaining information of the measured sample;
    (c) a first objective lens and a first lens being disposed on an optical path of a sample stage; and
    (d) a scanning mirror being disposed on an optical path in front of or at a rear of the polarization state generator, and operating to vary an incident angle of the polarized light beam emitted to the first lens, a position of the polarized light beam focused on the back focal plane of the first objective lens, and thus an angle of a light beam emitted to the sample from the first objective lens, thereby obtaining a scattering distribution image of the measured sample at different incident angles, and enabling rapid and accurate profile measurement of the measured sample in nanoscale by obtaining Mueller matrix at different scattered fields;

wherein:
    the measured sample on the sample stage is disposed at a front focal plane of the first objective lens, the polarized light beam emitted to the polarization state generator is focused on the back focal plane of the first objective lens via the first lens, and further on the measured sample via the first objective lens, light scattered from the measured sample is collected by the first objective lens and imaged on the back focal plane of the first objective lens, and then on an image acquisition device via the first lens and the polarization state analyzer.

2. The device of claim 1, wherein the scanning mirror is disposed at the rear of the polarization state generator so that incident light can be vertically emitted to the polarization state generator.

3. The device of claim 2, further comprising a beam splitter operating to reflect the polarized light beam, which is then emitted to the first lens.

4. The device of claim 3, wherein the first objective lens operating to collect scattered light is disposed on an optical path in front of the sample stage, and the back focal plane of the first objective lens coincides with the front focal plane of the first lens.

5. The device of claim 4, further comprising a second lens disposed on an optical path between the first lens and the polarization state analyzer, a back focal plane of the first lens coinciding with a front focal plane of the second lens.

6. A method for measuring a large-area and massive scattered field in nanoscale, the method comprising:
1) modulating an emergent light beam thereby obtaining a light beam with a polarization state;
2) demodulating an emitted polarized light beam containing information of a measured sample thereby obtaining information of the measured sample;
3) focusing the polarized light beam on a back focal plane of a first objective lens via a first lens, the first lens and the first objective lens being disposed on an optical path in front of a sample stage, the measured sample on the sample stage being disposed on a front focal plane of the first objective lens, light focused on the back focal plane being emitted to the measured sample via the first objective lens, light scattered from the measured sample being collected by the first objective lens and imaged on the back focal plane of the first objective lens, and then on an image acquisition device via the first lens and a polarization state analyzer; and
4) varying an incident angle of the polarized light beam emitted to the first lens, a position of the polarized light beam focused on the back focal plane of the first objective lens, and thus an angle of a light beam emitted to the sample from the first objective lens, thereby obtaining a scattering distribution image of the measured sample at different incident angles, and enabling rapid and accurate profile measurement of the measured sample in nanoscale by obtaining Mueller matrix at different scattered fields.

7. The method of claim 6, wherein variation of the incident angle is facilitated by a scanning mirror disposed on an optical path in front of or at the rear of the polarization state generator.

8. The method of claim 7, wherein the scanning mirror is disposed at the rear of the polarization state generator so that incident light can be vertically emitted to the polarization state generator.

9. The method of claim 8, wherein the polarized light beam is emitted to the first lens after being reflected by a beam splitter.

10. The method of claim 9, wherein the first objective lens operating to collect scattered light is disposed on an optical path in front of the sample stage, and the back focal plane of the first objective lens coincides with the front focal plane of the first lens.

11. The method of claim 10, wherein a second lens is disposed on an optical path between the first lens and the polarization state analyzer, and a back focal plane of the first lens coincides with a front focal plane of the second lens.

12. A device for measuring a large-area and massive scattered field, the device comprising:
(a) a polarization state generator being disposed on an output optical path of a laser source, and operating to modulate a light beam emitted thereon thereby obtaining a light beam with a polarization state;
(b) a polarization state analyzer operating to demodulate a polarized light beam emitted thereon and containing information of a measured sample thereby obtaining information of the measured sample;
(c) a first objective lens and a first lens being disposed on an optical path of a sample stage;
(d) a scanning mirror being disposed on an optical path in front of or at a rear of the polarization state generator, and operating to vary an incident angle of the polarized light beam emitted to the first lens, a position of the polarized light beam focused on the back focal plane of the first objective lens, and thus an angle of a light beam emitted to the sample from the first objective lens, thereby obtaining a scattering distribution image of the measured sample at different incident angles, and enabling rapid and accurate profile measurement of the measured sample in nanoscale by obtaining Mueller matrix at different scattered fields;
(e) a second objective lens disposed opposite to the sample stage; and
(f) a third lens disposed at the rear of the second objective lens, a back focal plane of the second objective lens coinciding with a focal plane of the third lens;
wherein:
the measured sample on the sample stage is disposed at a front focal plane of the first objective lens, the polarized light beam emitted to the polarization state generator is focused on the back focal plane of the first objective lens via the first lens, and further on the measured sample via the first objective lens to form scattered light;
the scattered light transmits the sample and is collected by the second objective lens.

13. The device of claim 12, further comprising a fourth lens disposed on an optical path between the third lens and the polarization state analyzer, a back focal plane of the third lens coinciding with a front focal plane of the fourth lens.

14. The device of claim 13, wherein the polarization state generator comprises a polarizer, a first compensator and a first servo motor sequentially disposed along an optical path, the polarizer operates to transform an incident light into linear polarized light, the first compensator operates to modulate the linear polarized light into a light with a polarization state, and the first servo motor operates to load uniform rotation of the first compensator.

15. The device of claim 14, wherein the polarization state analyzer comprises a second compensator, a second servo motor and a analyzer sequentially disposed along an optical path, the second compensator operates to demodulate the polarized light with a polarization state, the analyzer operates to modulate the demodulated polarized light into linear polarized light, and the second servo motor operates to load uniform rotation of the second compensator.

* * * * *